US012161786B2

United States Patent
Wellings et al.

(10) Patent No.: US 12,161,786 B2
(45) Date of Patent: Dec. 10, 2024

(54) DIALYSIS TRANSFER SET HAVING FILTER INTEGRITY TESTING

(71) Applicants: BAXTER INTERNATIONAL INC., Deerfield, IL (US); BAXTER HEALTHCARE SA, Glattpark (CH)

(72) Inventors: Anders Wellings, Belleair Beach, FL (US); Edward S. Szpara, St. Charles, IL (US); Michael P. Morrissey, Algonquin, IL (US)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 976 days.

(21) Appl. No.: 17/055,864

(22) PCT Filed: May 16, 2019

(86) PCT No.: PCT/US2019/032626
§ 371 (c)(1),
(2) Date: Nov. 16, 2020

(87) PCT Pub. No.: WO2019/222473
PCT Pub. Date: Nov. 21, 2019

(65) Prior Publication Data
US 2021/0220539 A1    Jul. 22, 2021

Related U.S. Application Data

(60) Provisional application No. 62/672,316, filed on May 16, 2018.

(51) Int. Cl.
*A61M 1/16*       (2006.01)
*A61M 1/14*       (2006.01)
*A61M 1/28*       (2006.01)

(52) U.S. Cl.
CPC ............ *A61M 1/1672* (2014.02); *A61M 1/14* (2013.01); *A61M 1/155* (2022.05);
(Continued)

(58) Field of Classification Search
CPC ........ A61M 1/14; A61M 1/16; A61M 1/1601; A61M 1/1656; A61M 1/1672;
(Continued)

(56) References Cited

U.S. PATENT DOCUMENTS

2017/0203027 A1    7/2017   Burbank et al.

FOREIGN PATENT DOCUMENTS

WO    WO 2010/027437 A2    3/2010
WO    WO 2016/049542 A2    3/2016

OTHER PUBLICATIONS

International Search Report; International Application No. PCT/US2019/032626 mailed Oct. 11, 2019—3 Pages.
(Continued)

*Primary Examiner* — John Kim
(74) *Attorney, Agent, or Firm* — K&L Gates LLP

(57) ABSTRACT

A dialysis system includes a source of water; a concentrate for mixing with the water a disposable set including a pumping portion, a water line in fluid including a filter for filtering the water, a concentrate line in fluid communication with the source of water and the pumping portion; and a medical fluid delivery machine including a pump actuator operable with the pumping portion, a pressure sensor, and a control unit programmed to cause (i) the pump actuator to pump water to wet a membrane of the filter, thereafter remove at least some of the water from the filter, and pressurize a portion of the water line leading from the pumping portion to the filter, (ii) the pressure sensor to sense pressure in the pressurized portion of the water line, and (iii)
(Continued)

an analysis of the sensed pressure to be performed to evaluate the integrity of the filter.

11 Claims, 5 Drawing Sheets

(52) U.S. Cl.
CPC ........ *A61M 1/1561* (2022.05); *A61M 1/1565* (2022.05); *A61M 1/159* (2022.05); *A61M 1/16* (2013.01); *A61M 1/1601* (2014.02); *A61M 1/1656* (2013.01); *A61M 1/28* (2013.01); *A61M 1/154* (2022.05); *A61M 2205/12* (2013.01); *A61M 2205/3331* (2013.01); *A61M 2205/705* (2013.01)

(58) Field of Classification Search
CPC .. A61M 1/155; A61M 1/1561; A61M 1/1565; A61M 1/159; A61M 1/154; A61M 1/28; A61M 2205/12; A61M 2205/3331; A61M 2205/705
See application file for complete search history.

(56) References Cited

OTHER PUBLICATIONS

Written Opinion of the International Searching Authority; International Application No. PCT/US2019/032626 mailed Oct. 11, 2019—5 Pages.

DIALYSIS TRANSFER SET HAVING FILTER INTEGRITY TESTING

RELATED APPLICATIONS

This application claims the benefit of and priority to U.S. Provisional Patent Application No. 62/672,316 filed May 16, 2018, entitled "DIALYSIS TRANSFER SET HAVING FILTER INTEGRITY TESTING," which is incorporated herein by reference in its entirety.

BACKGROUND

The present disclosure relates generally to medical fluid devices. More specifically, the present disclosure relates to medical fluid devices that mix fluid online for treatment or that receive fluid mixed online for treatment.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney function is critical to many people because the treatment is life saving.

One type of kidney failure therapy is hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD (HF, HDF) treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products than a patient receiving less frequent but perhaps longer treatments. A patient receiving more frequent treatments does not experience as much of a down cycle as does an in-center patient, who has built-up two or three day's worth of toxins prior to a treatment. In certain areas, the closest dialysis center may be many miles from the patient's home, causing door-to-door treatment time to consume a large portion of the day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal cavity. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid solution bags.

APD machines pump used or spent dialysate from the peritoneal cavity, though the catheter, and to the drain. As with the manual process, several drain, fill and dwell cycles occur during dialysis. A "last fill" may occur at the end of the APD treatment. The fluid may remain in the peritoneal cavity of the patient until the start of the next treatment, or may be manually emptied at some point during the day.

In any of the above modalities using an automated machine, treatment fluid may be prepared online or at the point of use, e.g., before and/or during the treatment. Here, purified water is typically mixed with a concentrate to prepare the treatment fluid online. To purify the water, a filter may be used. It is possible for the filter to become damaged. A need exists accordingly to provide a way to determine when the filter has become damaged, so that any potential harm to the patient resulting from the damaged filter may be avoided.

SUMMARY

The examples described herein disclose automated systems and methods applicable, for example, to fluid delivery for: peritoneal dialysis ("PD"), plasmapheresis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO") treatments. The systems and methods described herein are applicable to any medical fluid delivery system in which the treatment fluid may be made online or at the point of use, e.g., just before and/or during treatment. These modalities may be referred to collectively or generally individually herein as medical fluid delivery system(s).

Moreover, each of the systems and methods described herein may be used with clinical or home-based treatments. For example, the present systems and methods may be employed in in-center PD, HD, HF or HDF machines, which run throughout the day. Alternatively, the present systems and methods may be used with home PD, HD, HF or HDF machines, which are operated generally at the patient's convenience.

In one embodiment, a peritoneal dialysis system and method are provided having point of use dialysis fluid production. The system includes a cycler and a water purifier. The cycler includes a control unit having at least one processor and at least one memory. The cycler may further include a wired or wireless transceiver for sending information to and receiving information from the water purifier. The water purifier may also include a control unit having at least one processor and at least one memory and a wired or wireless transceiver for sending information to and receiving information from the control unit of the cycler.

The cycler includes equipment programmed via its control unit to prepare fresh dialysis solution at the point of use, pump the freshly prepared dialysis fluid to a patient, allow the dialysis fluid to dwell within the patient, then pump used dialysis fluid to a drain. The cycler in one embodiment includes a heater under control of the control unit for heating the dialysis fluid as it is being mixed in one embodiment. The heater may for example be located at the top of a housing of the cycler, e.g., beneath a heating lid.

The cycler (and the water purifier in one embodiment) operates with a disposable set. The disposable set in one embodiment includes a disposable pumping cassette, which may include a planar rigid plastic piece covered on one or both sides by a flexible membrane, forming fluid pumping and valving chambers. The fluid pump chambers may operate with pneumatic pump chambers of the cycler, while fluid valve chambers operate with the pneumatic valve chambers of the cycler.

The disposable set may include (i) a patient line that extends from the cassette to a patient line connector, (ii) a drain line that extends from the cassette to a drain line connector (which may in turn connect removeably to the water purifier), (iii) a heater/mixing line that extends from the pumping cassette to a heater/mixing bag of the present disclosure, (iv) an upstream water line segment that extends from the water purifier to a water accumulator and a downstream water line segment that extends from the water accumulator to the cassette, (v) a last bag or sample line that extends from the cassette to a premixed last fill bag of dialysis fluid or to a sample bag or other sample collecting container, (vi) a first, e.g., glucose, concentrate line extending from the cassette to a first, e.g., glucose, concentrate container, and/or (vii) a second, e.g., buffer, concentrate line that extends from the cassette to a second, e.g., buffer, concentrate container.

In an embodiment, the upstream water line segment includes one or more sterilizing grade filter that further filters water exiting the water purifier to ensure that the water is made suitable for a peritoneal dialysis treatment ("WFPD") in case the water purifier itself is not able to do so. Redundant sterilizing grade filters are provided in an embodiment in case one of the filters fails. An integrity test is performed to ensure that at least the downstream filter is intact and functioning properly prior to each treatment in one embodiment.

The upstream water line segment in one embodiment includes a first portion extending from the water purifier to the upstream sterilizing grade filter, a second portion extending from the upstream sterilizing grade filter to the downstream sterilizing grade filter, and a third portion extending from the downstream sterilizing grade filter to one leg of a Y-connector (or T-connector, or the like). A common leg of the Y-connector leads to and from the water accumulator. A third leg of the Y-connector connects to a downstream water line segment, which runs from the Y-connector to a port of the disposable cassette.

The Y-connector is advantageous for the integrity test mentioned above, which is performed on at least one of the sterilizing grade filters. The integrity test in one embodiment applies a negative pressure to the sterilizing grade filter. The Y-connector provides a passage for the negative pressure to reach the filter, wherein the passage bypasses and does not require the water accumulator. The water accumulator may seal closed under negative pressure, such that a passage that included the interior of the water accumulator would be prone to becoming blocked. The legs of Y-connector not extending to the water accumulator allow a clear passage for negative pressure to be applied by the pumping chambers of the disposable set to the sterilizing grade filter even if the water accumulator has collapsed closed under the negative pressure.

The integrity test is in one embodiment a pressure decay test in which one or more hydrophilic cleaning membrane of the filter is first wetted. Wetting the membrane prevents air from passing through the membrane if the membrane is intact. Next, a preset negative pressure is applied to the filter, wherein the pneumatic pathway leading to the filter is closed. If the membrane is intact and wetted properly, the negative pressure in the pneumatic pathway leading to the filter will hold, at least so that a measured pressure decay rate level is below a predetermined pressure decay rate setpoint. But if one or more membrane of the sterilizing grade filter has been compromised, then the negative pressure will pull air in through the compromised membrane, relieving the negative pressure at a measured rate above a predetermined pressure decay rate setpoint. When this occurs, the control unit of the cycler causes its user interface to alarm and in one embodiment provide an audio, visual or audiovisual message informing the patient or caregiver that the filter is likely compromised and instructing that the current disposable set be replaced with a new set.

It should be appreciated from above that a source of air to the one or more membrane of the sterilizing grade filter is needed to perform the integrity test. In one embodiment, the filter is provided with one or more hydrophobic vent that allows air but not liquid to pass though the vent. The vent(s) is(are) configured to prevent any particulates or contaminants in the air from entering the filter. In another embodiment, the hydrophobic vent is provided instead in a second Y-connector, T-connector or branch stemming from the upstream water line segment upstream of the sterilizing grade filter, e.g., in the second portion of the upstream water line segment located between the upstream and downstream sterilizing grade filters. In this alternative embodiment, the filters do not need to provide or be fitted with one or more hydrophobic vent.

The pressure decay test just described is a first integrity test. In an alternative embodiment, the control unit of the cycler and/or the control unit of the water purifier alternatively or additionally performs a second integrity test using the water purifier to interrogate the sterilizing grade filters. Here, the control unit of the cycler and/or the water purifier is configured to examine the ratio of purified water pressure to flow rate (or flow rate to pressure) to inspect the integrity of the sterilizing grade filters. The control unit of the water purifier may have the capability to monitor the ratio over an extended period and to detect changes in performance of the sterile sterilizing filters, compensating with greater or lower pressure and alerting the user as needed. The control unit of the water purifier may report results to the control unit of the cycler, which notifies the patient of any problem. In one implementation, the water purifier maintains a flow rate through the sterilizing grade filters. In doing so, the water purifier compensates (raises or lowers) the pressure at which purified water is delivered to maintain the constant flow rate. Should one or both filters be compromised or should a leak occur in the purified water pathway, the preset flow rate will be achieved at a lower pressure, which the water purifier is configured to measure. Conversely, should one or both filters become partially blocked for whatever reason (e.g., due to bioburden), the preset flow rate will be achieved at a higher pressure, which the water purifier is configured to measure. In either situation, by monitoring the purified water flow rate to pressure relatively, and comparing same to predetermined limits set in the control unit of the water purifier or the cycler, an undesirable sterilizing condition will be detected and alerted to the patient or caregiver, instructing same to replace the currently installed disposable set with a new set having new sterilizing grade filters.

In light of the disclosure herein and without limiting the disclosure in any way, in a first aspect of the present disclosure, which may be combined with any other aspect listed herein unless specified otherwise, a dialysis system includes: a source of water purified; a source of concentrate for mixing with water from the water source; a disposable set including a pumping portion, a water line in fluid communication with the source of water and the pumping portion, the water line including a filter for filtering the water, a concentrate line in fluid communication with the concentrate source and the pumping portion; and a medical fluid delivery machine including a pump actuator operable with the pumping portion of the disposable set, a pressure sensor, and a control unit configured to cause (i) a membrane of the filter to be wetted, (ii) the pump actuator to remove at least some of the water from the filter, (iii) a portion of the water line leading from the pumping portion to the filter to be pressurized, (iv) the pressure sensor to sense pressure in the pressurized portion of the water line, and (v) an analysis of the sensed pressure to be performed to evaluate the integrity of the filter.

In a second aspect of the present disclosure, which may be combined with any other aspect listed herein unless specified otherwise, the control unit is configured to cause the pump actuator to pressurize the portion of the water line leading from the pumping portion to the filter.

In a third aspect of the present disclosure, which may be combined with any other aspect listed herein unless specified otherwise, the portion of the water line leading from the pumping portion to the filter is pressurized under negative pressure.

In a fourth aspect of the present disclosure, which may be combined with any other aspect listed herein unless specified otherwise, the pump actuator is a pneumatic pump actuator, the pumping portion of the disposable cassette includes a flexible pumping sheet, and wherein pressurizing the portion of the water line includes pneumatically moving the flexible pumping sheet.

In a fifth aspect of the present disclosure, which may be combined with the fourth aspect in combination with any other aspect listed herein unless specified otherwise, the dialysis system includes at least one of a positive or negative source of pressurized air operable with a pneumatic side of the membrane, and wherein the pressure sensor is located between the source of pressurized air and the pneumatic side of the membrane.

In a sixth aspect of the present disclosure, which may be combined with any other aspect listed herein unless specified otherwise, the pump actuator is a peristaltic pump actuator, the pumping portion of the disposable cassette includes a portion of the water line extending to operate with the peristaltic pump actuator, and wherein the pressure sensor is positioned and arranged to operate with a portion of the tube leading from the peristaltic pump actuator to the filter.

In a seventh aspect of the present disclosure, which may be combined with the sixth aspect in combination with any other aspect listed herein unless specified otherwise, the peristaltic pump actuator is configured to pressurize the water line leading from the pumping portion to the filter under negative pressure.

In an eighth aspect of the present disclosure, which may be combined with any other aspect listed herein unless specified otherwise, the source of water includes a water purifier, and wherein a pump of the water purifier is caused to wet the membrane of the filter.

In a ninth aspect of the present disclosure, which may be combined with the eighth aspect in combination with any other aspect listed herein unless specified otherwise, the water purifier includes a control unit, and wherein the control unit of the medical fluid delivery machine communicates with the control unit of the water purifier to command the pump of the water purifier to wet the membrane of the filter.

In a tenth aspect of the present disclosure, which may be combined with any other aspect listed herein unless specified otherwise, the control unit causes the pump actuator of the medical fluid delivery machine to wet the membrane of the filter.

In an eleventh aspect of the present disclosure, which may be combined with any other aspect listed herein unless specified otherwise, wetting the membrane of the filter includes causing water to be pumped across the membrane at least one time.

In a twelfth aspect of the present disclosure, which may be combined with any other aspect listed herein unless specified otherwise, a dialysis system includes: a source of water purified; a source of concentrate for mixing with water from the water source; a disposable set including a pumping portion, a concentrate line in fluid communication with the source of concentrate and the pumping portion, a water line in fluid communication with the source of water and the pumping portion, the water line including a filter for filtering the water, a water accumulator in fluid communication with the water line via a connection that enables fluid communication between the pumping portion and the filter even if fluid communication with the water accumulator is occluded; and a medical fluid delivery machine including a pump actuator operable with the pumping portion of the disposable set to apply a negative pressure to the filter to evaluate the integrity of the filter even if the water accumulator is occluded due to the negative pressure.

In a thirteenth aspect of the present disclosure, which may be combined with the twelfth aspect in combination with any other aspect listed herein unless specified otherwise, the pump actuator is operable with the pumping portion of the disposable set to apply the negative pneumatic pressure to the filter to evaluate the integrity of the filter even if the water accumulator is occluded due to the negative pneumatic pressure.

In a fourteenth aspect of the present disclosure, which may be combined with the twelfth aspect in combination with any other aspect listed herein unless specified otherwise, the disposable set further includes a drain line, and wherein the pump actuator is operable with the pumping portion to remove water from the filter via the drain line prior to applying the negative pressure to the filter to evaluate the integrity of the filter.

In a fifteenth aspect of the present disclosure, which may be combined with the fourteenth aspect in combination with any other aspect listed herein unless specified otherwise, the source of water includes a water purifier, and wherein the water removed form the filter to drain is supplied to the filter from the water purifier.

In a sixteenth aspect of the present disclosure, which may be combined with the fourteenth aspect in combination with any other aspect listed herein unless specified otherwise, the filter is a first filter, and which includes a second filter located in the water line upstream from the first filter, wherein the water removed form the first filter to drain is delivered through the second filter to the first filter.

In a seventeenth aspect of the present disclosure, which may be combined with any other aspect listed herein unless specified otherwise, a disposable set includes: a pumping portion; a concentrate line in fluid communication with the pumping portion; a water line in fluid communication with the pumping portion, the water line including a filter for filtering the water; a water accumulator in fluid communication with the water line via a multi-legged connection that enables fluid communication between the pumping portion and the filter through first and third legs of the connection even if fluid communication with the water accumulator via a second leg of the connection is occluded; and a structure enabling air to enter the filter and pass through a wetted membrane of the filter if compromised to evaluate the integrity of the filter.

In an eighteenth aspect of the present disclosure, which may be combined with the seventeenth aspect in combination with any other aspect listed herein unless specified otherwise, the structure enabling air to enter the filter includes at least one hydrophobic vent provided by the filter.

In a nineteenth aspect of the present disclosure, which may be combined with the seventeenth aspect in combination with any other aspect listed herein unless specified otherwise, the structure enabling air to enter the filter includes a hydrophobic vent placed in fluid communication with the water line.

In a twentieth aspect of the present disclosure, which may be combined with the seventeenth aspect in combination with any other aspect listed herein unless specified otherwise, the multi-legged connection includes a Y-connector or a T-connector.

In a twenty-first aspect of the present disclosure, any of the structure, functionality and alternatives disclosed in connection with FIGS. 1 to 6 may be combined with any of the other structure, functionality and alternatives disclosed in connection with FIGS. 1 to 6.

In light of the present disclosure and the above aspects, it is therefore an advantage of the present disclosure to provide an improved medical fluid delivery system.

It is another advantage of the present disclosure to provide an improved medical fluid delivery system that prepares treatment fluid online or at the point of use.

It is a further advantage of the present disclosure to provide an improved mixing structure and methodology for a medical fluid delivery system that prepares treatment fluid online or at the point of use.

It is yet another advantage of the present disclosure to provide an improved apparatus, system and method for testing the integrity of sterilizing grade filters used to prepare injectable grade medical solutions online.

It is a further advantage of the present disclosure to provide a second integrity test to evaluate the sterilizing grade filters in a different way to achieve different results that may be cross-meshed with the results of the first integrity test.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

The examples described herein are applicable to any medical fluid therapy system that delivers a medical fluid that may be mixed at the point of use, prior to and/or during treatment, such as dialysis fluid, substitution fluid, or an intravenous drug. The examples are particularly well suited for kidney failure therapies, such as all forms of peritoneal dialysis ("PD"), hemodialysis ("HD"), hemofiltration ("HF"), hemodiafiltration ("HDF") and continuous renal replacement therapies ("CRRT"), referred to herein collectively or generally individually as renal failure therapy. Moreover, the machines described herein may be used in clinical or home settings. For example, the machines and associated methods may be employed in an in-center PD or HD machine, which runs virtually continuously throughout the day. Alternatively, the machine and methods may be used in a home PD or HD machine, which can for example be run at night while the patient is sleeping. The machines and methods discussed herein are also applicable to medical delivery applications. The following examples will be described in the setting of a peritoneal dialysis system having point of use dialysis fluid production but may instead be used to make point of use treatment fluid for any of the above modalities.

Figure 1:
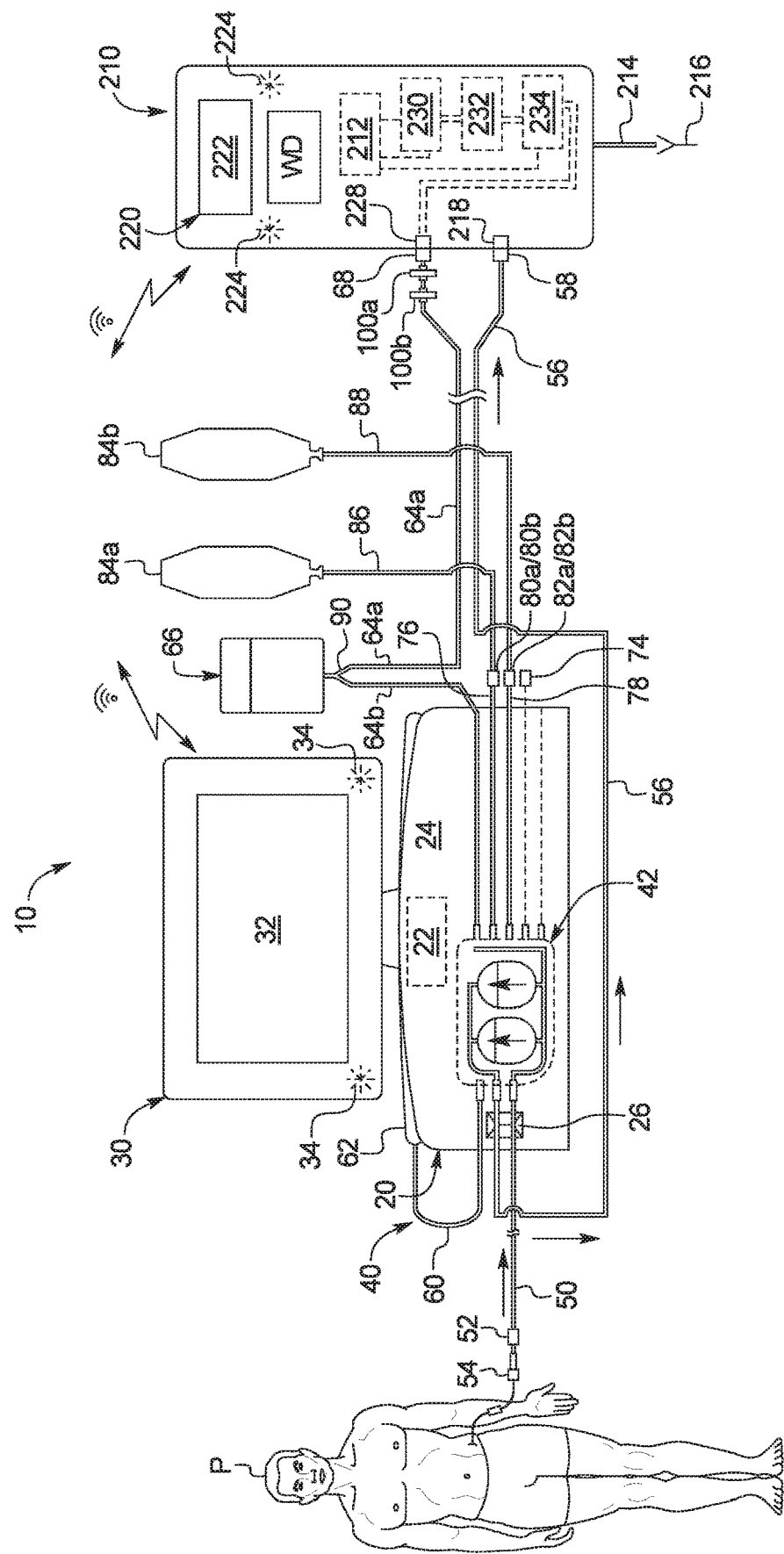
FIG. 1 is a front elevation view of one embodiment of a medical fluid delivery system having point of use dialysis fluid production of the present disclosure.

Referring now to the drawings and in particular to FIG. 1, one embodiment of a peritoneal dialysis system having point of use dialysis fluid production of the present disclosure is illustrated by system 10. System 10 includes a medical fluid delivery machine or cycler 20 and a water purifier 210. Suitable cyclers for cycler 20 include, e.g., the Amia® or HomeChoice® cycler marketed by Baxter International Inc., with the understanding that those cyclers are provided with updated programming to perform and use the point of use dialysis fluid produced according to system 10. To this end, cycler 20 includes a control unit 22 having at least one processor and at least one memory. Control unit 22 further incudes a wired or wireless transceiver for sending information to and receiving information from a water purifier 210. Water purifier 210 also includes a control unit 212 having at least one processor and at least one memory. Control unit 212 further incudes a wired or wireless transceiver for sending information to and receiving information from control unit 22 of cycler 20. Wired communication may be via Ethernet connection, for example. Wireless communication may be performed via any of Bluetooth™, WiFi™, Zigbee®, Z-Wave®, wireless Universal Serial Bus ("USB"), or infrared protocols, or via any other suitable wireless communication technology.

Cycler 20 includes a housing 24, which holds equipment programmed via control unit 22 to prepare fresh dialysis solution at the point of use, pump the freshly prepared dialysis fluid to patient P, allow the dialysis fluid to dwell within patient P, then pump used dialysis fluid to a drain. In the illustrated embodiment, water purifier 210 includes a drain line 214 leading to a drain 216, which can be a house drain or a drain container. The equipment programmed via control unit 22 to prepare fresh dialysis solution at the point of use in an embodiment includes equipment for a pneumatic pumping system, including but not limited to (i) one or more positive pressure reservoir, (ii) one or more negative pressure reservoir, (iii) a compressor and a vacuum pump each under control of control unit 22, or a single pump creating both positive and negative pressure under control of control unit 22, to provide positive and negative pressure to be stored at the one or more positive and negative pressure reservoirs, (iv) plural pneumatic valve chambers for delivering positive and negative pressure to plural fluid valve chambers, (v) plural pneumatic pump chambers for delivering positive and negative pressure to plural fluid pump chambers, (vi) plural electrically actuated on/off pneumatic solenoid valves under control of control unit 22 located between the plural pneumatic valve chambers and the plural fluid valve chambers, (vii) plural electrically actuated variable orifice pneumatic valves under control of control unit 22 located between the plural pneumatic pump chambers and the plural fluid pump chambers, (viii) a heater under control of control unit 22 for heating the dialysis fluid as it is being mixed in one embodiment, and (ix) an occluder 26 under control of control unit 22 for closing the patient and drain lines in alarm and other situations.

In one embodiment, the plural pneumatic valve chambers and the plural pneumatic pump chambers are located on a front face or surface of housing 24 of cycler 20. The heater is located inside housing 24 and in an embodiment includes heating coils that contact a heating pan or tray, which is located at the top of housing 24, beneath a heating lid (not seen in FIG. 1).

Cycler 20 in the illustrated embodiment includes a user interface 30. Control unit 22 in an embodiment includes a video controller, which may have its own processing and memory for interacting with primary control processing and memory of control unit 22. User interface 30 includes a video monitor 32, which may operate with a touch screen overlay placed onto video monitor 32 for inputting commands via user interface 30 into control unit 22. User interface 30 may also include one or more electromechanical input device, such as a membrane switch or other button. Control unit 22 may further include an audio controller for playing sound files, such as voice activation commands, at one or more speaker 34.

Water purifier 210 in the illustrated embodiment also includes a user interface 220. Control unit 212 of water purifier 210 in an embodiment includes a video controller, which may have its own processing and memory for interacting with primary control processing and memory of control unit 212. User interface 220 includes a video monitor 222, which may likewise operate with a touch screen overlay placed onto video monitor 222 for inputting commands into control unit 212. User interface 220 may also include one or more electromechanical input device, such as a membrane switch or other button. Control unit 212 may further include an audio controller for playing sound files, such as alarm or alert sounds, at one or more speaker 224 of water purifier 210.

Figure 2:
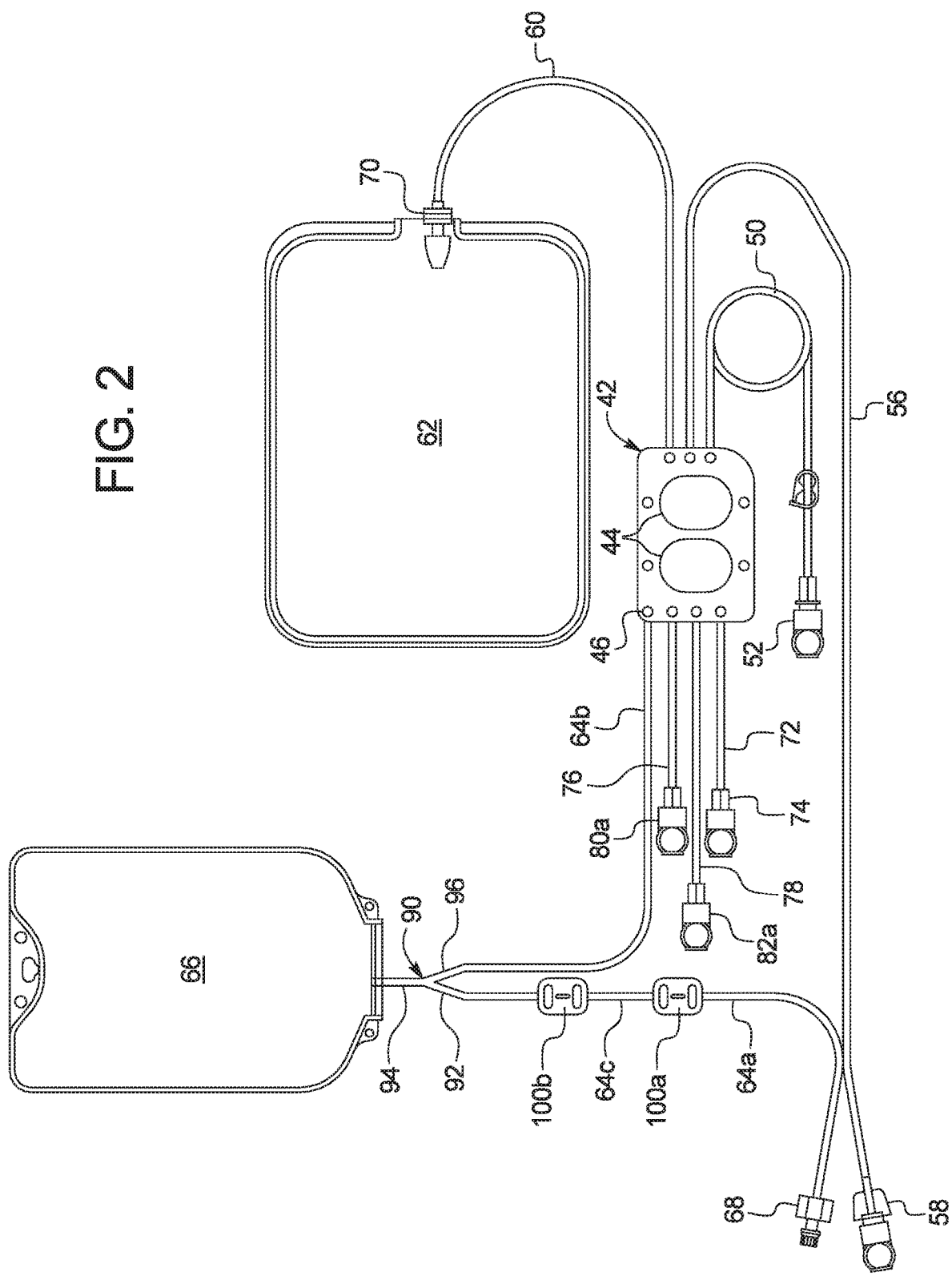
FIG. 2 is an elevation view of one embodiment of a disposable set used with the system illustrated in FIG. 1.

Referring additionally to FIG. 2, one embodiment of disposable set 40 is illustrated. Disposable set 40 is also illustrated in FIG. 1, mated to cycler 20 to move fluid within the disposable set 40, e.g., to mix dialysis fluid as discussed herein. Disposable set 40 in the illustrated embodiment includes a disposable cassette 42, which may include a planar rigid plastic piece covered on one or both sides by a flexible sheet 48. Flexible sheet 48 pressed against housing 24 of cycler 20 forms a pumping and valving membrane. FIG. 2 illustrates that disposable cassette 42 includes fluid pump chambers 44 that operate with the pneumatic pump chambers located at housing 24 of cycler 20 and fluid valve chambers 46 that operate with the pneumatic valve chambers located at housing 24 of cycler 20.

FIGS. 1 and 2 illustrate that disposable set 40 includes a patient line 50 that extends from a patient line port of cassette 42 and terminates at a patient line connector 52. FIG. 1 illustrates that patient line connector 52 connects to a patient transfer set 54, which in turn connects to an indwelling catheter located in the peritoneal cavity of patient P. Disposable set 40 includes a drain line 56 that extends from a drain line port of cassette 42 and terminates at a drain line connector 58. FIG. 1 illustrates that drain line connector 58 connects removeably to a drain connector 218 of water purifier 210.

FIGS. 1 and 2 further illustrate that disposable set 40 includes a heater/mixing line 60 that extends from a heater/mixing line port of cassette 42 and terminates at a heater/mixing bag 62. Disposable set 40 includes an upstream water line segment 64a that extends to a water inlet leg 92 of a Y-connector 90 (or T-connector, or the like) located just upstream of water accumulator 66. Y-connector 90 connects to water accumulator 66 via leg 94. A downstream water line segment 64b extends from a water outlet leg 96 of Y-connector 90 to cassette 42. In the illustrated embodiment, upstream water line segment 64a begins at a water line connector 68 and is located upstream from water accumulator 66. FIG. 1 illustrates that water line connector 68 is removeably connected to a water outlet connector 228 of water purifier 210.

Water purifier 210 outputs water and possibly water suitable for peritoneal dialysis ("WFPD"). To ensure WFPD, however, a sterilizing grade filter 100a is placed upstream from a downstream sterilizing grade filter 100b, respectively. Filters 100a and 100b may be placed in water line segment 64a upstream of water accumulator 66. Sterilizing grade filters 100a and 100b may be pass-through filters that do not have a reject line. Pore sizes for the hydrophilic membranes of filters 100a and 100b may, for example, be less than a micron, such as 0.1 or 0.2 micron. Suitable sterilizing grade filters 100a and 100b may be provided by the assignee of the present disclosure. In an embodiment, only one of upstream or downstream sterilizing grade filter 100a and 100b is needed to produce WFPD, nevertheless, two sterilizing grade filters 100a and 100b are provided in the illustrated embodiment for redundancy in case one fails. Sterilizing grade filters 100a and 100b are discussed in detail below.

FIG. 2 further illustrates that a last bag or sample line 72 may be provided that extends from a last bag or sample port of cassette 42. Last bag or sample line 72 terminates at a connector 74, which may be connected to a mating connector of a premixed last fill bag of dialysis fluid or to a sample bag or other sample collecting container. Last bag or sample line 72 and connector 74 may be used alternatively for a third type of concentrate if desired.

FIGS. 1 and 2 illustrate that disposable set 40 includes a first, e.g., glucose, concentrate line 76 extending from a first concentrate port of cassette 42 and terminates at a first, e.g., glucose, cassette concentrate connector 80a. A second, e.g., buffer, concentrate line 78 extends from a second concentrate port of cassette 42 and terminates at a second, e.g., buffer, cassette concentrate connector 82a.

FIG. 1 illustrates that a first concentrate container 84a holds a first, e.g., glucose, concentrate, which is pumped from container 84a through a container line 86 to a first container concentrate connector 80b, which mates with first cassette concentrate connector 80a. A second concentrate container 84b holds a second, e.g., buffer, concentrate, which is pumped from container 84b through a container line 88 to a second container concentrate connector 82b, which mates with second cassette concentrate connector 82a.

In an embodiment, to begin treatment, patient P loads cassette 42 into cycler and in a random or designated order (i) places heater/mixing bag 62 onto cycler 20, (ii) connects upstream water line segment 64a to water outlet connector 228 of water purifier 210, (iii) connects drain line 56 to drain connector 218 of water purifier 210, (iv) connects first cassette concentrate connector 80a to first container concentrate connector 80b, and (v) connects second cassette concentrate connector 82a to second container concentrate connector 82b. At this point, patient connector 52 is still capped. Once fresh dialysis fluid is prepared and verified, patient line 50 is primed with fresh dialysis fluid, after which patient P may connect patient line connector 52 to transfer set 54 for treatment. Each of the above steps may be illustrated graphically at video monitor 32 and/or be provided via voice guidance from speakers 34.

For disposable set 40, the rigid portion of cassette 42 may be made for example of a thermal olefin polymer of amorphous structure ("TOPAS") cyclic olefin copolymer ("coc"). The flexible membranes of cassette 42 may be made for example of a copolyletser ether ("PCCE") and may be of one or more layer. Any of the tubing or lines and Y-connector 90 may be made for example of polyvinyl chloride ("PVC"). Any of the connectors may be made for example of acrylonitrile-butadiene-styrene ("ABS", e.g., for Y-connector 90 (alternatively), for connector 70 of heater/mixing bag or container 62 and/or for concentrate connectors 80a, 80b, 82a, 82b discussed below), acrylic (e.g., for drain line connector 58) or PVC (e.g., for water line connector water line connector 68). Any of the bags or containers, such as heater/mixing bag or container 62 discussed below, may be made of PVC. The materials for any of the above components may be changed over time.

Control unit 22 may be programmed to cause cycler 20 to perform one or more mixing action to help mix dialysis fluid properly and homogeneously for treatment. For example, any of fluid pump chambers 44 may be caused to withdraw into the pump chambers some amount of mixed fluid (e.g., made from one or both first and second concentrates 84a, 84b and WFPD) from heater/mixing bag 62 and send such mixture back to heater/mixing bag 62 and repeat this procedure multiple times (described herein as a mixing sequence or "waffling"). In particular, to perform a mixing sequence, control unit 22 in an embodiment causes cycler 20 to close all fluid valve chambers 46 at cassette 42 except for the fluid valve chamber 46 to heater/mixing line 60 and heater/mixing bag 62. Fluid pump chambers 44 are stroked sequentially and repeatedly (i) pulling a possibly unmixed fluid combination of WFPD and concentrates from heater/mixing bag 62 into the pump chambers, followed by (ii) pushing the mixed WFPD and concentrates from the pump chambers back to heater/mixing bag 62 and (iii) repeating (i) and (ii) at least one time. Control unit 22 may be programmed to stroke fluid pump chambers 44 together so that they both pull and push at the same time, or alternatingly so that one pump chamber 44 pulls from heater/mixing bag 62, while the other pump chamber 44 pushes to heater/mixing bag 62, creating turbulence in heater/mixing line 60.

Providing heater/mixing container or bag 62 with cassette 42 via heater/mixing line 60 enables the WFPD from accumulator 66 and concentrates from first and second concentrate containers 84a and 84b to be at least partially mixed prior to entering container or bag 62. Even if cassette 42 is not provided, the WFPD and at least one concentrate will mix partially in heater/mixing line 60 prior to reaching the container or bag.

Sterile Filters

Figure 3:
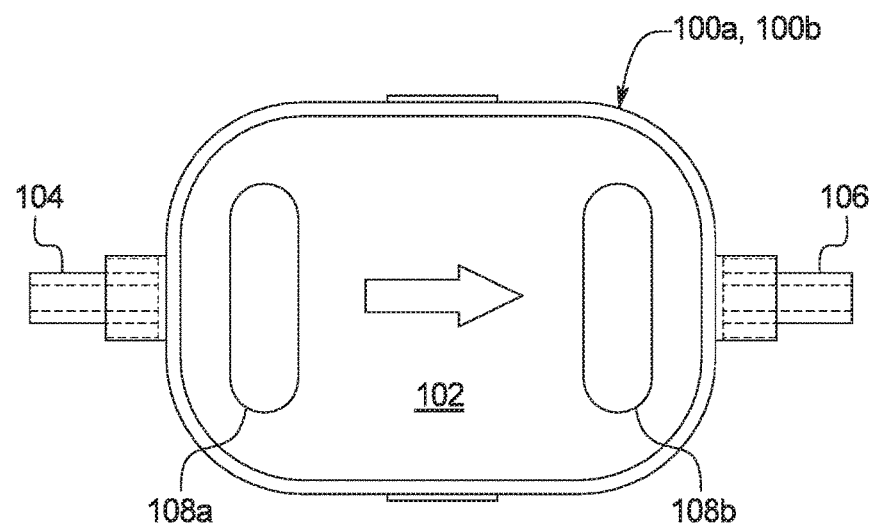
FIG. 3 is a top plan view of one embodiment of a sterile filter of the present disclosure for purifying the water used for make dialysis fluid for treatment.
Figure 4:
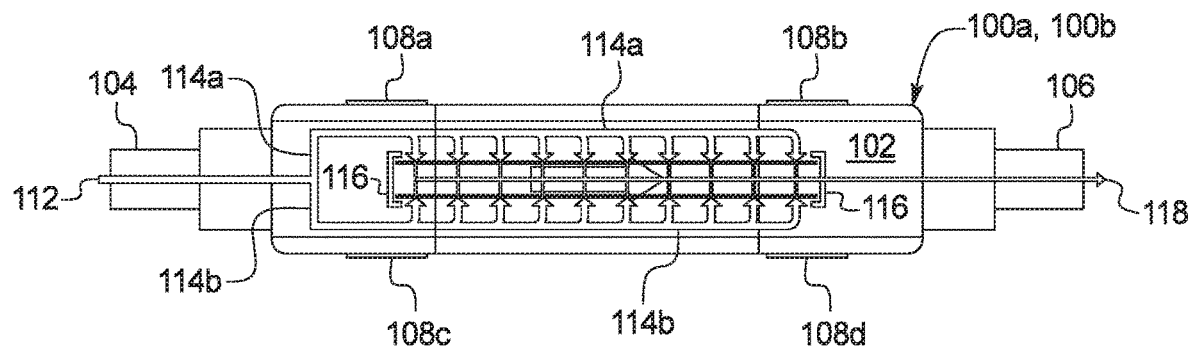
FIG. 4 is a schematic elevation sectioned view of the embodiment of the sterilizing grade filter of FIG. 3.

Referring now to FIGS. 3 and 4, sterilizing grade filters 100a and 100b are illustrated in more detail. Sterilizing grade filters 100a and 100b may, for example, be Pall IV-5 or GVS Speedflow filters, or be filters provided by the assignee of the present disclosure. Filters 100a and 100b include a housing 102, which may be made of any medical grade polymer, such as any of the materials listed above. Housing 102 includes or defines a filter inlet 104 and a filter outlet 106. Filter inlet 104 of upstream sterilizing grade filter 100a is connected sealingly, e.g., via a compression, hose barb, or luer connection, to the upstream-most section of upstream water line segment 64a, while filter outlet 106 of upstream sterilizing grade filter 100a is connected sealingly, e.g., via a compression, hose barb, or luer connection, to a section 64c (FIG. 5) of upstream water line segment 64a located between filters 100a and 100b. Filter inlet 104 of downstream sterilizing grade filter 100b is connected sealingly, e.g., via a compression, hose barb, or luer connection, to section 64c (FIG. 5) of upstream water line segment 64a, while filter outlet 106 of downstream sterilizing grade filter 100b is connected sealingly, e.g., via a compression, hose barb, or luer connection, to a downstream-most section of upstream water line segment 64a.

FIGS. 3 and 4 also illustrate that housing 102 includes one or more hydrophobic filter or vent 108a to 108d. Hydrophobic materials are air passing but liquid, e.g., water, retaining, such that air may pass through vents 108a to 108d, but wherein the vents prevent liquid from entering into and flowing out of housing 102. Vents 108a to 108d serve the purpose of allowing air to enter filters 100a and 100b and in doing so, removing particulates and contaminants from the air so that the entering air does not affect the liquid or water flowing through the filter 100a or 100b. Multiple vents 108a to 108d are advantageous because they provide multiple pathways for air in case one or more of vents 108a to 108d becomes wetted, which prevents air from passing across the hydrophobic vents.

FIG. 4 illustrates how water flows through the illustrated embodiment for filters 100a and 100b. Water enters though inlet 104 and flows along an inlet path 112. Inlet path 112 splits into inlet branches 114a and 114b. Inlet branch 114a extends above a hydrophilic membrane 110a, while inlet branch 114b extends below a hydrophilic membrane 110b in the orientation of filter 100a, 100b in FIG. 4. Hydrophilic materials are liquid passing and air retaining when wetted. Hydrophilic membranes 110a and 110b accordingly allow liquid to pass through, while not allowing air to pass through when wetted with liquid, thereby preventing air entering filters 100a and 100b from becoming entrained in the water traveling through the filters. Pore sizes for hydrophilic membranes 110a and 110b may again, for example, be less than a micron, such as 0.1 or 0.2 micron.

In the illustrated embodiment, hydrophilic membranes 110a and 110b are provided as part of a membrane housing 116. Membrane housing 116 is sealed to hydrophilic membranes 110a and 110b, so that the only way into the inside of housing 116 is through the membranes. In this manner, when hydrophilic membranes 110a and 110b are wetted properly with a liquid, e.g., purified water, such that the membranes block air flow, no air may enter membrane housing 116 from the outside of the housing.

FIG. 4 illustrates that water filtered via hydrophilic membranes 110a and 110b leaves membrane housing 116 and exits outlet 106 of housing 102 via an outlet path 118. Water exiting via outlet path 118 after being purified by water purifier 210 and further filtered via filter 100a, 100b is considered to be pure enough to be WFPD. Again, one filter 100a, 100b is typically enough to ensure WFPD quality, however, two filters 100a and 100b may be provided for redundancy.

In an alternative embodiment, hydrophobic filter or vent 108a to 108d may not be provided with filters 100a and 100b and be provided instead adjacent to the filters. Filters 100a and 100b in such a case, would still provide one or more hydrophilic membrane 110a, 110b, but not the hydrophobic vents.

Filter Integrity Test

Figure 5:
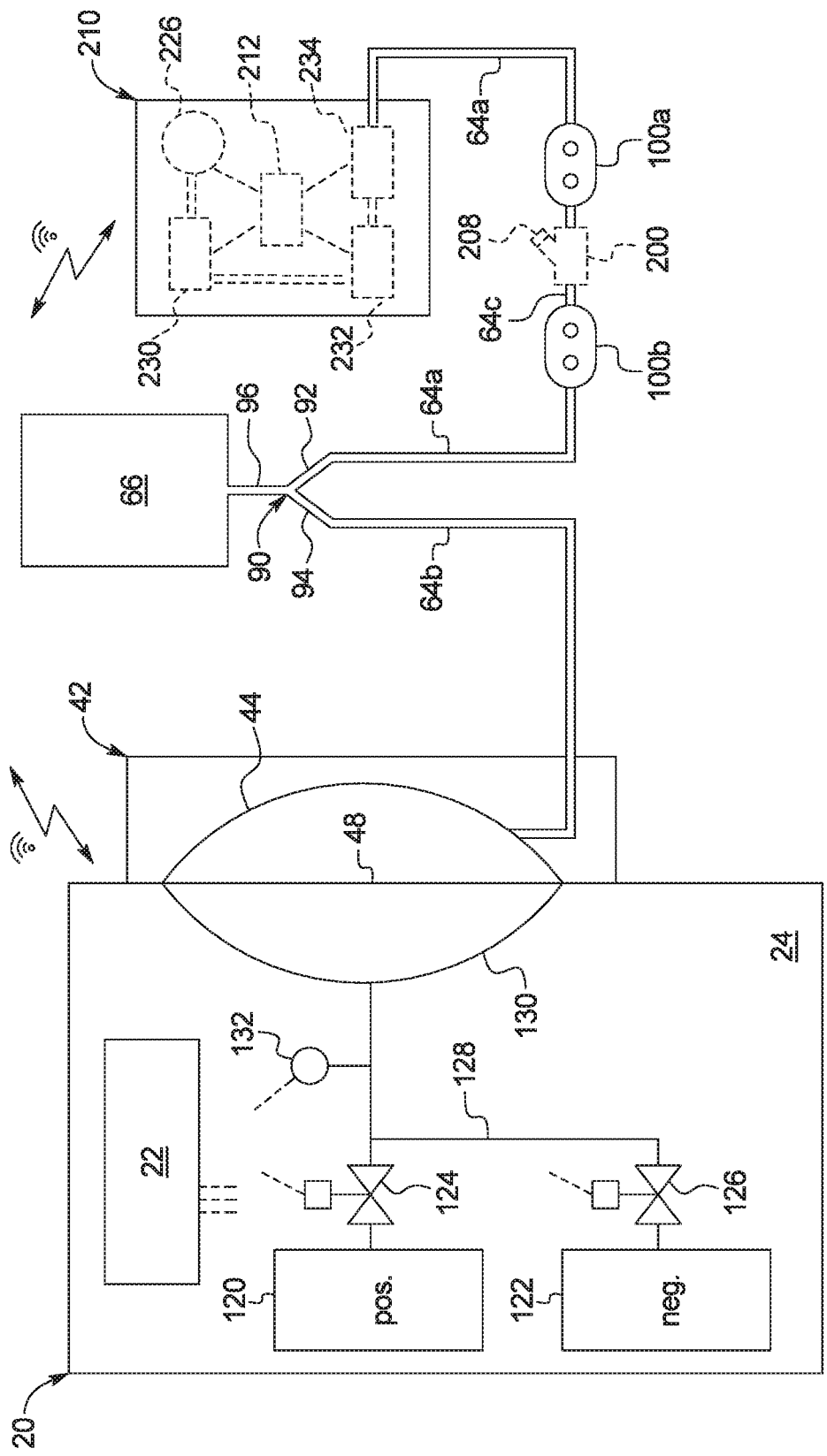
FIG. 5 is a schematic view of one embodiment of a fluid and pneumatic pathway extending from inside of the medical fluid delivery machine or cycler to the sterilizing grade filters.

Referring now to FIG. 5, one set of components from system 10 for performing a filter integrity test of the present disclosure is illustrated. FIG. 5 illustrates a simplified version of medical fluid delivery machine or cycler 20 having housing 24 holding control unit 22. Disposable cassette 42 is mounted operably to housing 24. Disposable cassette 42 receives WFPD from water purifier 210 having control unit 222, which communicates via wired or wireless communication (wireless shown) with control unit 22 of medical fluid delivery machine or cycler 20. Purified water leaving water purifier exits via upstream water line segment 64a, though filters 100a and 100b, ensuring WFPD, and in normal operation fills water accumulator 66 via legs 92 and 96 of Y-connector 90 (or T-connector, or the like) and with an associated water line valve 46 (not illustrated in FIG. 5) of cassette 42 closed, so that the WFPD backfills water accumulator 66. When the water line valve 46 of cassette 42 is opened, WFPD may flow between legs 92 and 94 of Y-connector 90, bypassing water accumulator 66, such that purified water may flow back and forth between cassette 42 and water purifier 210 via upstream water line segment 64a and downstream water line segment 64b.

Components in FIG. 5 not illustrated in FIG. 4 include positive and negative pressure reservoirs 120 and 122, respectively, located within medical fluid delivery machine or cycler 20. Medical fluid delivery machine 20 is in one embodiment actuated pneumatically. Positive and negative pressure reservoirs 120 and 122 may be charged via one or more pneumatic pump (not illustrated), wherein positive tank 120 may hold, e.g., three to seven +psig air, while negative tank 122 may hold, e.g., one to six −psig air. Positive and negative pressure reservoirs 120 and 122 communicate via electrically actuated pneumatic solenoid valves 124 and 126, respectively, located along pneumatic lines 128 with a pneumatic pump chamber 130 defined in or provided by housing 24 of machine 20. Electrically actuated pneumatic solenoid valves 124 and 126 in an embodiment are closed when unenergized and opened upon being energized.

A pressure sensor 132 is located along pneumatic line 128. The dashed lines extending from control unit 22, solenoid valves 124 and 126 and pressure sensor 132 indicate that solenoid valves 124 and 126 and pressure sensor 132 may receive power and/or signals from control unit 22 and may send electrical or signal readings to control unit 22. The dashed lines extending from control unit 222 and water pump 226 of water purifier 210 likewise indicate that control unit 222 may electrically control water pump 226 and receive electrical or signal feedback from water pump 226.

FIG. 5 illustrates that disposable cassette 42 in one embodiment includes a flexible sheet 48 that covers fluid pump chambers 44 of the cassette. Flexible sheet 48 may also cover one or more fluid valve 46 (not illustrated in FIG. 5) of disposable cassette 42. To push fluid out of disposable cassette 42, control unit 22 causes pneumatic solenoid valve 124 to open, enabling flexible sheet 48 at pump chamber 44 to see positive pressure, which pushes flexible sheet 48 towards the wall of fluid pump chamber 44, and expels fluid from disposable cassette 42, e.g., out downstream water line segment 64b. To pull fluid into disposable cassette 42, control unit 22 causes pneumatic solenoid valve 126 to open, enabling flexible sheet 48 at pump chamber 44 to see negative pressure, which pulls flexible sheet 48 towards the wall of pneumatic pump chamber 130, thereby pulling fluid into disposable cassette 42, e.g., from downstream water line segment 64b.

In both the inlet (negative) and outlet (positive) strokes discussed above, pressure sensor 132 monitors the pressure in pneumatic line 128. Due to the flexibility of sheet 48, the pneumatic pressure sensed at pressure sensor 132 is the same as the fluid pressure located on the opposite side of the sheet. In this way, if the negative pneumatic pressure for pumping from the patient is controlled to be, e.g., −1.5 psig, the fluid pressure exerted on the patient is likewise −1.5 psig. If the positive pneumatic pressure for pumping to the patient is controlled to be, e.g., +3.0 psig, the fluid pressure exerted on the patient is likewise +3.0 psig.

Figure 6:
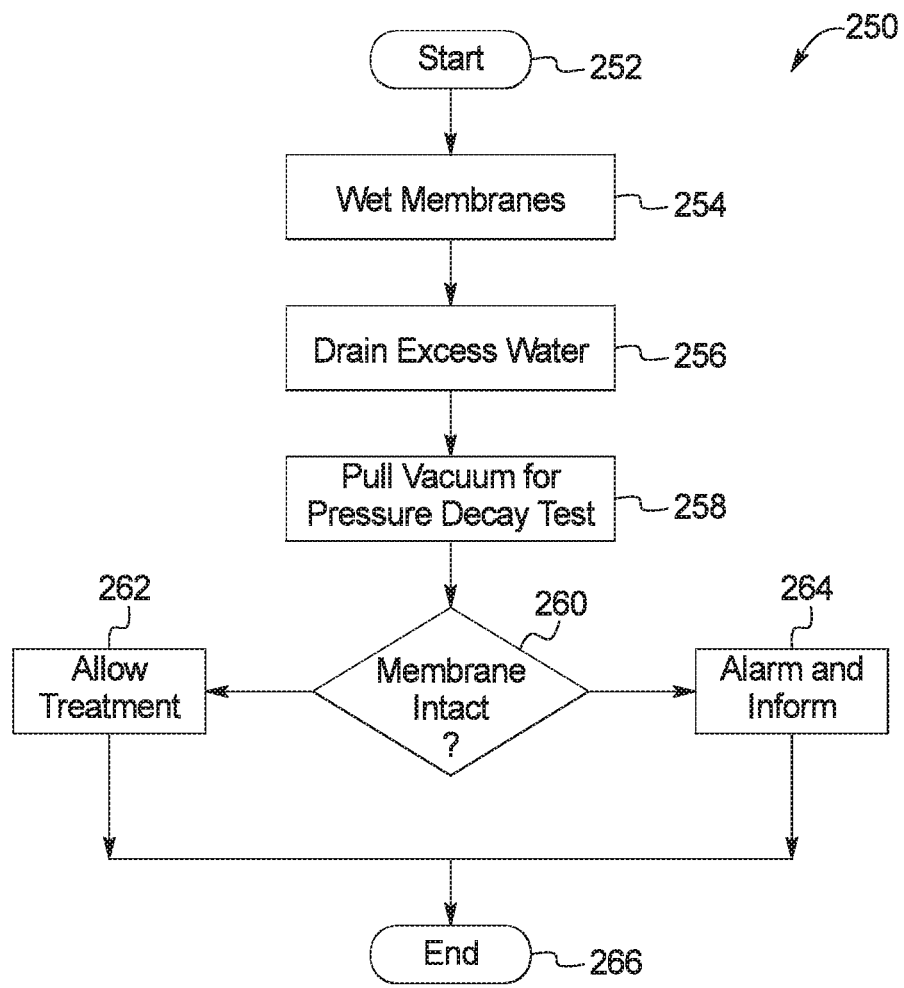
FIG. 6 is a schematic flow diagram illustrating one embodiment of an integrity test procedure of the present disclosure using the fluid and pneumatic pathway of FIG. 5.

Referring additionally to FIG. 6, one embodiment of an integrity test procedure of the present disclosure is illustrated via method 250. Method 250 is controlled in one embodiment via control unit 22 of machine or cycler 20, which may as needed communicate with control unit 222 of water purifier 210. At oval 252, method 250 begins. Method 250 is a method for testing the integrity of sterilizing grade filters 100a and 100b, and in one embodiment downstream sterilizing grade filter 100b. As such, method 250 is performed in one embodiment prior to each treatment. In an alternative embodiment, to conserve time, method 250 may be performed while dialysis fluid is mixing and being heated in heater/mixing bag 62. Here, if a compromised sterilizing grade filter 100b is detected, the mixing dialysis fluid may be discarded along with disposable set 40. Further alternatively of additionally, if disposable set 40 is to be reused, method 250 may be performed after treatment, which would allow set 40 to be changed if needed prior to beginning the next treatment.

When method 250 is performed prior to treatment, disposable set 40 is initially dry. As discussed above in connection with FIG. 4, to close off membrane housing 116 from outside air, hydrophilic membranes 110a and 110b need to be wetted, as illustrated at block 254. To wet membranes 110a and 110b, machine control unit 22 in one embodiment communicates with purifier control unit 222, prompting control unit 222 to cause pump 226 to pump an amount of purified water from water purifier 210 sufficient to fully wet the membranes 110a and 110b of downstream sterilizing grade filter 100b. It should be appreciated that doing so also wets the membranes 110a and 110b of upstream sterilizing grade filter 100a. Water may be pumped back and forth across membranes 110a and 110b one or more time to fully wet the membranes.

At block 256, control unit 22 sequences pneumatic valves 124 and 126 and the water and drain fluid valves 46 of disposable cassette 42 in an attempt to pull water that has been pushed in wetting step 254 passed downstream sterilizing grade filter 100b into cassette 42 and to push the fluid out of the disposable cassette to drain via drain line 56. It should be appreciated that the drained water is allowed to bypass water accumulator 66 via legs 92 and 96 of Y-connector 190. At the end of the drain sequence of block 256, it is desirable for a clear pneumatic path to exist between pump chamber(s) 44 of disposable cassette 42 and downstream sterilizing grade filter 100b.

Because sterilizing grade filter 100b is vented via hydrophobic vents 108a to 108d, when cycler 20 pulls a vacuum on water line segments 64a and 64b, the vacuum will pull air in through the vents to pull the purified water back through water line segments 64a and 64b to cassette 42. The purified water will pass through hydrophilic membranes 110a and 110b so long as the vacuum is applied. Once the water is evacuated from filter 100b, air will try to pass through hydrophilic membranes 110a and 110b. If membranes 110a and 110b are wetted out with water, air will not be allowed to pass unless the bubble point of membranes 110a and 110b is reached, which should never happen with intact membranes because the bubble point is selected to be sufficiently high. If a hole has developed in either membrane 110a or 110b, air will continue to displace purified water in upstream water line segment 64a towards Y-connector 90. It is worth noting that if filter 100b closest to accumulator bag 66 does not have a compromised hydrophilic membrane 110a or 110b, the pressure decay test will pass even if there is a hole in either hydrophilic membrane 110a or 110b of upstream filter 100a (closest to the water purifier 210) because any air that enters through hydrophobic vents 108a to 108d of upstream filter 100a will be trapped at the intact hydrophilic membranes 110a and 110b of downstream filter 100b, and the vacuum pulled via cycler 20 will be maintained.

At block 258, control unit 22 causes a pressure decay test on the membranes 110a and 110b of downstream sterilizing grade filter 100b to be initiated. To initiate the pressure decay test, control unit 22 closes (or keeps closed) positive pneumatic valve 126 and opens negative pneumatic valve 124 to pull a vacuum on flexible sheet 48 and correspondingly on the air in downstream water line segment 64b, Y-connector 90, upstream water line segment 64a, and the inside of membrane housing 116 holding the wetted hydrophilic membranes 110a and 110b of downstream filter 100b. In an embodiment, flexible sheet 48 is pulled only part of the way towards the wall of pneumatic pump chamber 130. Although not illustrated, it is contemplated to place one or more pneumatic regulator, e.g., a variable orifice pneumatic regulator, in pneumatic line 128 upstream of pressure sensor 132. The pneumatic regulator allows control unit 22 to set a desired positive or negative pressure in pneumatic line 128 between the regulator and pneumatic pump chamber 130. In this manner, the negative pressure for the pressure decay test of block 258 may be set at a desired negative pressure, e.g. −5 psig., which is confirmed via pressure sensor 132.

After the desired negative pressure has been set, control unit 22 at diamond 260 monitors readings from pressure sensor 132 to see if the negative pressure holds. That is, if wetted hydrophilic membranes 110a and 110b are in tact, then no or very little air may enter membrane housing 116 via hydrophobic filter or vent 108a to 108d. If, however, one or more wetted hydrophilic membrane 110a and 110b is not in tact, e.g., if there is a tear in one of the membranes, then air will enter into the otherwise closed membrane housing 116 via hydrophobic filter or vent 108a to 108d. The additional air will relieve the vacuum on the fluid side of flexible sheet 48. Flexible sheet 48 will move responsively to equalize the negative pressure on both sides. Since the negative pressure is temporarily higher on the pneumatic side of flexible sheet 48, the sheet will move towards the wall of pneumatic pump chamber 130, thereby relieving negative pressure in pneumatic line 128, which is sensed by pressure sensor 132 and signaled to control unit 22.

At diamond 260, control unit 22 looks at pressure signals from pressure sensor 132 over a predetermined amount of time for the pressure decay test. The predetermined amount of time may be, for example, on the order of minutes, e.g., one to five minutes or seconds, e.g., 15 to 60 seconds. If the negative pressure loss or decay amounts to more than a preset threshold, then control unit 22 determines that there is a leaking membrane 110a and/or 110b in downstream sterilizing grade filter 100b. The leakage may be programmed into control unit 22 as a rate of decay expressed in units of pressure over time. Here, leakage rate above a rate threshold triggers a compromised hydrophilic membrane determination.

In one example, water purifier 210 delivers a small volume of purified water through each filter 110a and 100b to wet out each hydrophilic membrane 110a and 110b as discussed above. A product water valve at purifier 210 is closed at water purifier 210 and cycler 20 begins to evacuate the water and air from water lines 64a and 64b until a vacuum pressure stabilizes at 25 kPa, which is enough to collapse water accumulator 66 (desirable for the pressure decay test) but not the tubing of water line segments 64a and 64b. Cycler 20 then stops pulling the vacuum and begins to monitor the negative pressure in water lines 64a and 64b, which may last for up to twenty seconds. During this time, if the pressure drop across any two second window is A 0.12 kPa/sec*2 sec=Δ 0.24 kPa or more, then cycler 20 assumes and error in hydrophilic membrane 110a or 110b of downstream filter 100b and reacts as described herein.

It all should be appreciated that negative pressure supplied during each of the steps associated with block 256, block 258 and diamond 260 is able to reach filter 100b even if the negative pressure closes and occludes water accumulator 66. Y-connector 190 allows accumulator 66 to be bypassed in such a case as described herein.

At block 262, if control unit 22 determines that downstream sterilizing grade filter 100b is intact, then control unit 22 continues treatment. At block 264, if control unit 22 determines that downstream sterilizing grade filter 100b is compromised, then control unit 22 discontinues treatment, alarms audibly, visually or audiovisually, and alerts the patient or caregiver to remove current disposable set 40 and to install a new set to continue treatment. At oval 266, method 250 ends.

It should be appreciated that even if downstream sterilizing grade filter 100b is determined to be compromised, it is highly likely that upstream sterilizing grade filter 100a is still intact. So if for example the failed integrity test is performed after treatment, the treatment has nevertheless been performed in all probability using properly sterilized dialysis fluid.

FIG. 5 illustrates in phantom an alternative embodiment in which a connector 200 housing one or more hydrophobic filter or vent 208 is located between upstream and downstream sterilizing grade filters 100a and 100b at section 64c. Here, filters 100a and 100b do not need hydrophobic vents 108a to 108d. If one or more wetted hydrophilic membrane 110a and 110b of downstream sterilizing grade filter 100b is not in tact, e.g., if a tear exists in one of the membranes, then air will enter into the otherwise closed membrane housing 116 via hydrophobic vent 208.

Alternative or Additional Integrity Test

The pressure decay test just described is a first integrity test. In an alternative embodiment, control unit 22 of cycler 20 and/or control unit 212 of water purifier 210 alternatively or additionally performs a second integrity test using equipment 230, 232 and 234 of water purifier 210 to interrogate sterilizing grade filters 100a and 100b. Here, control unit 22 of cycler 20 and/or control unit 212 of water purifier 210 is/are configured to examine the ratio of the pressure to flow rate (or flow rate to pressure) to inspect the integrity of the hydrophilic membranes 110a and 110b of both sterilizing grade filters 100a and 100b.

In various embodiments, control unit 212 of the water purifier 210 has the capability to monitor the ratio over an extended period and to detect changes in performance of hydrophilic membranes 110a and 110b of sterilizing grade filters 100a and 100b, compensating with greater or lower pressure and alerting the user as needed. Control unit 212 of water purifier 210 may (i) report results to control unit 22 of the cycler 20, which notifies the patient of any problem via user interface 30 or (ii) report results at user interface 220 of water purifier 210 for notification.

In one implementation, water purifier 210 maintains a purified water flow rate through the sterilizing grade filters 100a and 100b using an electronic flow meter 230 outputting to control unit 212. In doing so, water purifier 210 compensates (raises or lowers) the pressure at which purified water is delivered to maintain the constant flow rate set in control unit 212 using an electronic pressure regulator 232 under command of control unit 212 and an electronic pressure gauge outputting to control unit 212. Should one or both filters 100a and 100b be compromised or should a leak occur in the purified water line segments 64a and 64b, the preset flow rate measured at flow meter 230 will be achieved at a lower pressure, which the water purifier 210 controls via regulator 232 and measures via gauge 234. Conversely, should one or both filters 100a and 100b become partially blocked for whatever reason (e.g., due to bioburden), the preset flow rate measured at flow meter 230 will be achieved at a higher pressure, which water purifier 210 controls via regulator 232 and measures via gauge 234. In either situation, by monitoring the flow rate to pressure relatively at control unit 212, and comparing same to predetermined limits set in the control unit of water purifier 210 or that of cycler 20, an undesirable sterilizing condition is detected and alerted to the patient or caregiver, instructing same to replace the currently installed disposable set 40 with a new set having new sterilizing grade filters 100a and 100b.

As discussed, the alternative flow rate/pressure integrity test just described may be used alternatively or additionally to the pressure decay test described at method 230 of FIG. 6. When used additionally, it should be appreciated that sterilizing grade filters 100a and 100b are tested from both downstream (pressure decay) and upstream (flow rate/pressure) directions. The pressure decay and flow rate/pressure tests also compliment each other in that the pressure decay test pinpoints downstream filter 100b as the culprit, while the flow rate/pressure test determines if either filter 100a and 100b fails. Thus if the flow rate/pressure test fails but the pressure decay test passes, then it may be assumed that upstream filter 100a is the culprit.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, while the pump actuator is described as being controlled by the control unit to pressurize the water line portion leading to the wetted filter, it is possible to alternatively connect that portion to a separate source of pressure in a valved manner, the separate source being for example a separate air pump or a separate container of pressurized air. Also, while the pressure sensor has been described as being the pressure sensor used with the pump actuator, it is contemplated to alternatively use a separate pressure sensor, e.g., a separate non-invasive pressure sensor coupled directly to the water line portion leading to the wetted filter. Further, while the present disclosure has been described primarily in connection with pneumatic pump, it is contemplated to instead use a different type of pump, such as a peristaltic pump operable with a pumping tube leading upstream to one or more sterilizing grade filter, and wherein the peristaltic pump is configured to place a negative pressure on the filter. Moreover, while the disposable set is described herein as having a water accumulator, and wherein the water purifier pumps water to the filters and the water purifier, in alternative embodiments (i) the medical fluid delivery machine or cycler may instead pump water into the water accumulator and/or the filters to wet the filters or (ii) the water accumulator is not provided and either one or both of the water purifier and/or the medical fluid delivery machine or cycler pumps water to wet at least one membrane of at least one sterilizing grade filter.

The invention is claimed as follows:

1. A dialysis system comprising:
   a source of water purified;
   a source of concentrate for mixing with water from the water source;
   a disposable set including
      a pumping portion,
      a water line in fluid communication with the source of water and the pumping portion, the water line including a filter for filtering the water,
      a concentrate line in fluid communication with the concentrate source and the pumping portion; and
   a medical fluid delivery machine including
      a pump actuator operable with the pumping portion of the disposable set,
      a pressure sensor, and
      a control unit configured to cause (i) a membrane of the filter to be wetted, (ii) the pump actuator to remove at least some of the water from the filter, (iii) a portion of the water line leading from the pumping portion to the filter to be pressurized, (iv) the pressure sensor to sense pressure in the pressurized portion of the water line, and (v) an analysis of the sensed pressure to be performed to evaluate an integrity of the filter.

2. The dialysis system of claim 1, wherein the control unit is configured to cause the pump actuator to pressurize the portion of the water line leading from the pumping portion to the filter.

3. The dialysis system of claim 1, wherein the portion of the water line leading from the pumping portion to the filter is pressurized under negative pressure.

4. The dialysis system of claim 1, wherein the pump actuator is a pneumatic pump actuator, the pumping portion of a disposable set includes a flexible pumping sheet, and wherein pressurizing the portion of the water line includes pneumatically moving the flexible pumping sheet.

5. The dialysis system of claim 4, which includes at least one of a positive or negative source of pressurized air operable with a pneumatic side of the membrane, and wherein the pressure sensor is located between the source of pressurized air and the pneumatic side of the membrane.

6. The dialysis system of claim 1, wherein the pump actuator is a peristaltic pump actuator, the pumping portion of a disposable set includes a portion of the water line extending to operate with the peristaltic pump actuator, and wherein the pressure sensor is positioned and arranged to operate with a portion of the water line leading from the peristaltic pump actuator to the filter.

7. The dialysis system of claim 6, wherein the peristaltic pump actuator is configured to pressurize the water line leading from the pumping portion to the filter under negative pressure.

8. The dialysis system of claim 1, wherein the source of water includes a water purifier, and wherein a pump of the water purifier is caused to wet the membrane of the filter.

9. The dialysis system of claim 8, wherein the water purifier includes a control unit, and wherein the control unit of the medical fluid delivery machine communicates with the control unit of the water purifier to command the pump of the water purifier to wet the membrane of the filter.

10. The dialysis system of claim 1, wherein the control unit causes the pump actuator of the medical fluid delivery machine to wet the membrane of the filter.

11. The dialysis system of claim 1, wherein wetting the membrane of the filter includes causing water to be pumped across the membrane at least one time.

* * * * *